(12) United States Patent
Stokes et al.

(10) Patent No.: US 10,682,137 B2
(45) Date of Patent: Jun. 16, 2020

(54) SURGICAL STAPLER

(71) Applicant: Ethicon LLC, Guaynabo, PR (US)

(72) Inventors: Michael J. Stokes, Cincinnati, OH (US); Chester O. Baxter, III, Loveland, OH (US); Nathan D. Grubbs, Cincinnati, OH (US); Laura Boehm, Hamilton, OH (US)

(73) Assignee: Ethicon LLC, Guaynabo, PR (US)

( * ) Notice: Subject to any disclaimer, the term of this patent is extended or adjusted under 35 U.S.C. 154(b) by 109 days.

(21) Appl. No.: 15/679,194

(22) Filed: Aug. 17, 2017

(65) Prior Publication Data
US 2018/0055512 A1    Mar. 1, 2018

Related U.S. Application Data

(60) Provisional application No. 62/380,746, filed on Aug. 29, 2016.

(51) Int. Cl.
*A61B 17/072*    (2006.01)
*A61B 17/28*    (2006.01)
(Continued)

(52) U.S. Cl.
CPC ...... *A61B 17/072* (2013.01); *A61B 17/07207* (2013.01); *A61B 17/2833* (2013.01);
(Continued)

(58) Field of Classification Search
CPC ............... A61B 17/068; A61B 17/072; A61B 17/07207; A61B 17/00234;
(Continued)

(56) References Cited

U.S. PATENT DOCUMENTS 5,893,506 A * 4/1999 Powell ............... A61B 17/072
227/175.1
5,894,979 A * 4/1999 Powell ............... A61B 17/072
227/175.2
(Continued)

FOREIGN PATENT DOCUMENTS

WO    WO 9523557 A1    9/1995
WO    WO 2013109445 A2    7/2013
(Continued)

OTHER PUBLICATIONS

Extended European Search Report and Written Opinion dated Oct. 25, 2017 for EP App. No. 17188357.2 (9 pages).
(Continued)

*Primary Examiner* — Scott A Smith

(57) ABSTRACT

A surgical instrument can be provided as described herein. The surgical instrument can include a handle with first and second handle portions. One of the first and second housing portions can include a proximal latch and a proximal latch pin. The proximal latch and proximal latch pin can be configured to lock the first and second housing portions together at proximal ends thereof. One of the first and second housing portions can further include a latch projection, a clamp arm, an over center linkage where the latch projection and over center linkage can be configured to lock the surgical instrument in a closed position when the clamp arm is engaged or in an engaged position.

9 Claims, 16 Drawing Sheets

(51) Int. Cl.
*A61B 17/00* (2006.01)
*A61B 17/068* (2006.01)
*A61B 17/29* (2006.01)

(52) U.S. Cl.
CPC ......... *A61B 17/068* (2013.01); *A61B 17/2909* (2013.01); *A61B 2017/0053* (2013.01); *A61B 2017/00477* (2013.01); *A61B 2017/07214* (2013.01); *A61B 2017/07278* (2013.01); *A61B 2017/07285* (2013.01)

(58) Field of Classification Search
CPC .......... A61B 2017/07214; A61B 2017/00477; A61B 17/2833; A61B 2017/046; A61B 2017/00367
USPC .. 227/19, 175.1, 175.2, 175.3, 176.1, 180.1; 606/139, 213, 219
See application file for complete search history.

(56) References Cited

U.S. PATENT DOCUMENTS

| | | | |
|---|---|---|---|
| 6,783,524 | B2 | 8/2004 | Anderson et al. |
| 7,766,209 | B2 | 8/2010 | Baxter, III et al. |
| 7,954,686 | B2 | 6/2011 | Baxter, III et al. |
| 2009/0308907 | A1* | 12/2009 | Nalagatla ......... A61B 17/07207 227/175.2 |
| 2014/0353357 | A1* | 12/2014 | Agarwal ........... A61B 17/07207 227/176.1 |
| 2016/0262756 | A1* | 9/2016 | Patankar .......... A61B 17/07207 |
| 2017/0143335 | A1* | 5/2017 | Gupta ............... A61B 17/07207 |

FOREIGN PATENT DOCUMENTS

WO  WO 2015065482 A1  5/2015
WO  WO 2015174985 A1  11/2015

OTHER PUBLICATIONS

International Search Report and Written Opinion dated Oct. 25, 2017 for App. No. PCT/US2017/048341 (14 pages).

* cited by examiner

SURGICAL STAPLER

CROSS REFERENCE TO RELATED APPLICATIONS

This application claims the benefit of U.S. Provisional Application 62/380,746, filed on Aug. 29, 2016, the content of which is incorporated by reference herein in its entirely.

BACKGROUND

Currently, surgeons use stapling instruments to suture body tissues such as a lung, an esophagus, a stomach, a duodenum and/or other organs in the intestinal tract. The use of an appropriate stapling instrument can perform a better job in less time and simplify previously difficult surgical procedures such as gastrointestinal anastomoses. One of those stapling instruments can include a linear cutting stapler or linear cutter. A linear cutting stapler or liner cutter can be used in surgical operations for wound closure, and internal tissue closure and excision. A typical linear cutting stapler can staple and cut such that redundant tissue can be removed (e.g., by the cut) and the wound can be closed (e.g., by the stapler). Such a linear cutting stapler generally includes two jaws (i.e., an upper jaw and a lower jaw), a clamp or closing handle for clamping or closing the upper jaw and the lower jaw, a staple anvil and a staple cartridge arranged opposite to each other at the front ends or distal end of the upper jaw and lower jaw respectively, a firing piece and a cutter which are arranged in the staple cartridge and are moveable synchronously relative to the staple cartridge, and an actuator or firing mechanism for driving movement of the firing piece and the cutter. Typically, staples are arranged in the staple cartridge, the firing piece pushes a staple pusher successively and pushes the staples towards the staple anvil, and the cutter cuts off the tissue between the staple cartridge and the staple anvil. Unfortunately, in current linear cutting staplers or linear cutters, the jaws can come decoupled or can be hard to assemble prior to use when performing a procedure, clamping can be difficult on thicker tissue, and operation thereof can be difficult with two hands, let alone one hand.

SUMMARY

A surgical instrument such as a linear cutter or stapler can be provided. In examples, the surgical instrument can limit the maximum jaw aperture as well as can be configured for single handed clamping and use as described herein. Further, in examples, housing portions and/or jaws (e.g., an anvil and/or staple cartridge that may be part of or may be the jaws) of the surgical instrument and can form and end-effector thereof can remain coupled via a latch such as proximal latch and components associated therewith and housing portions and jaws can be moved from an open position to a closed position such that tissue can be clamped, stapled and incised via a clamp arm and components associated therewith.

Figure 1:
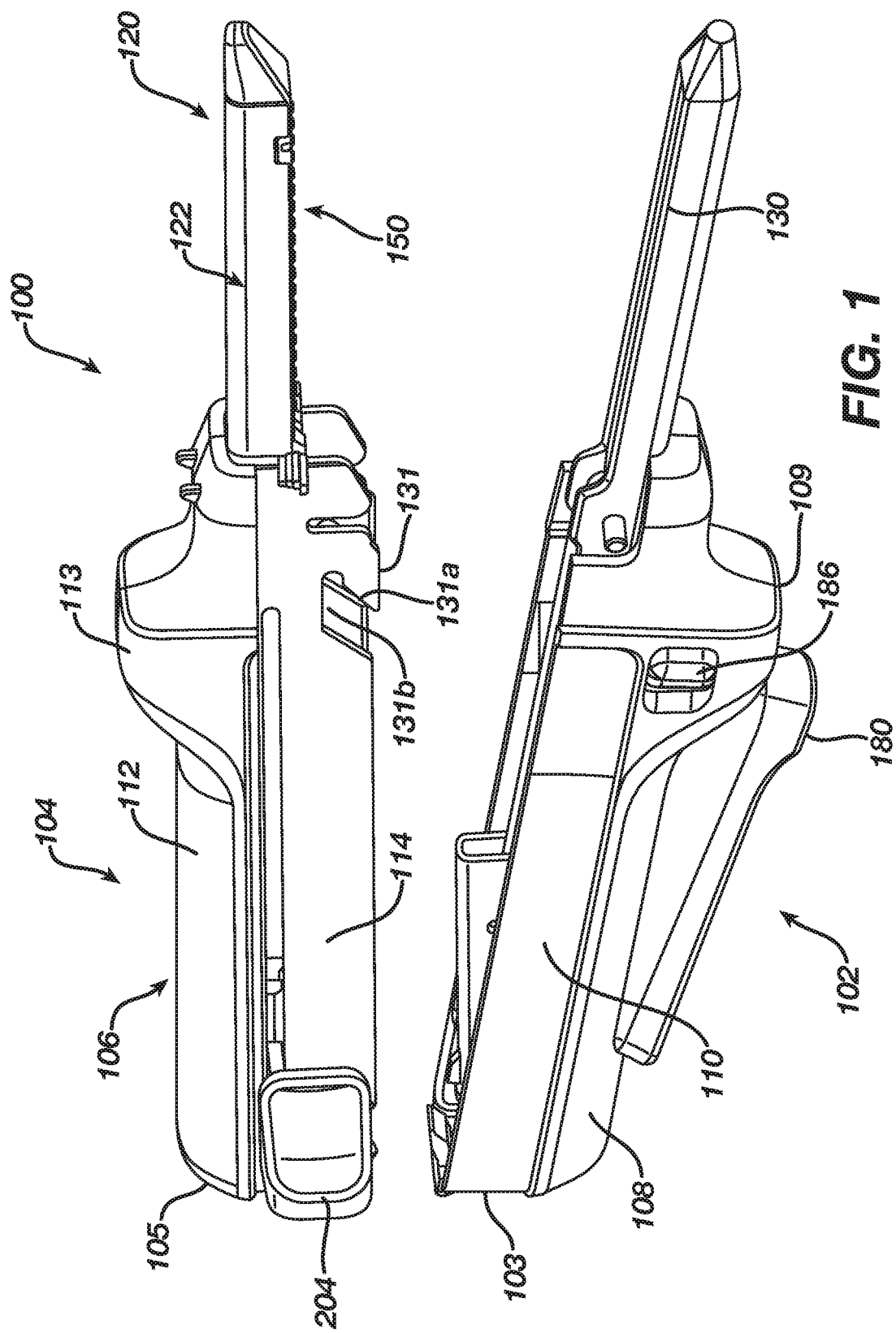
FIGS. 1-11 illustrate a surgical stapling instrument in accordance with one or more examples herein.
Figure 2:
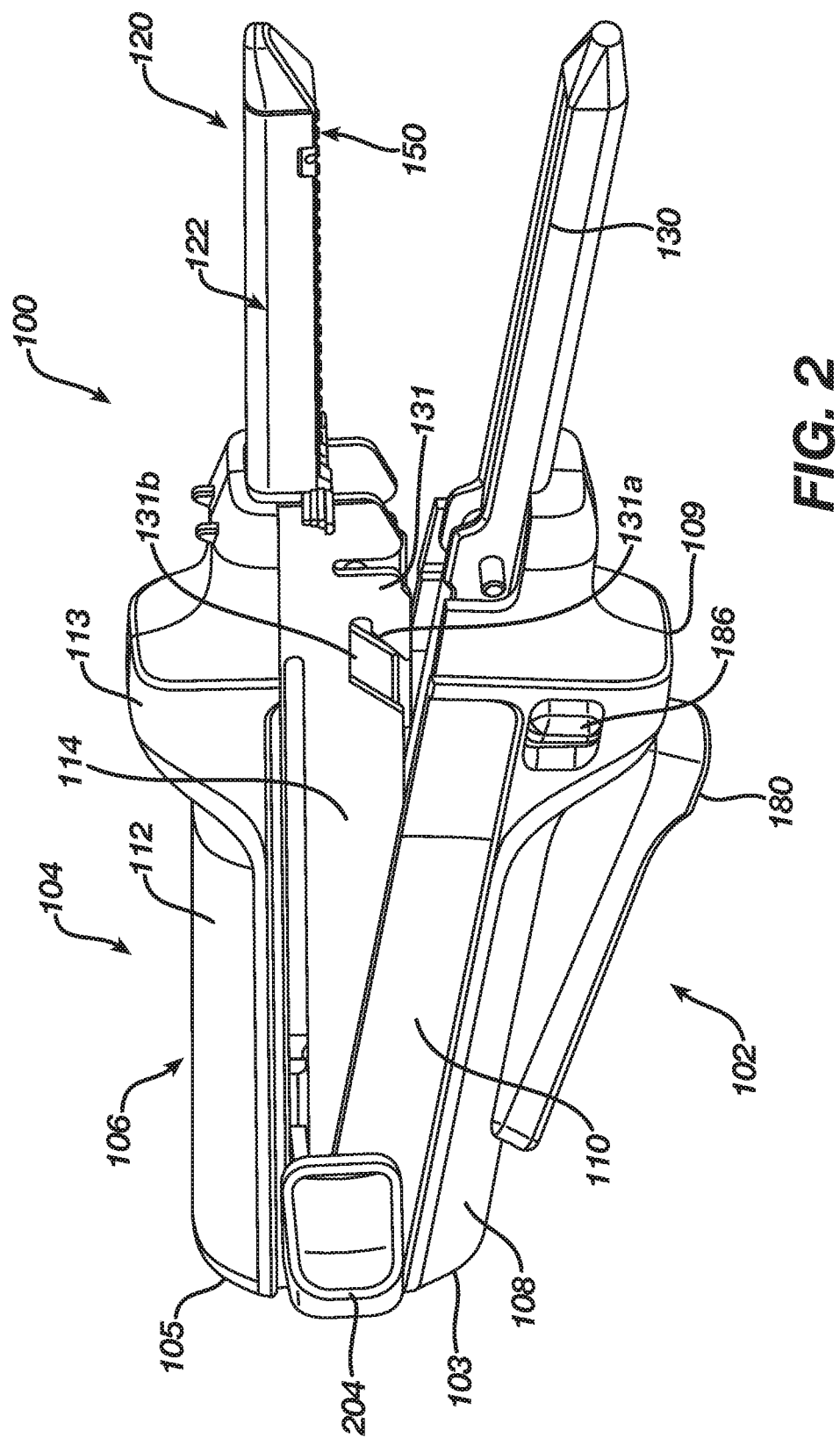

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal," "distal," "upper," and "lower" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. The terms "proximal," "distal," "upper," and "lower" are thus relative terms and not intended to unnecessarily limit the invention described herein.

FIGS. 1-11 illustrate a surgical stapling instrument 100 (e.g., also referred herein as a linear cutter or stapler 100) in accordance with one or more examples herein. As shown in FIG. 1, the surgical stapling instrument 100, generally, can comprise a first handle portion 102 and a second handle portion 104. In various examples, the first handle portion 102 and second handle portion 104 can be configured to be grasped by a surgeon, for example, and can comprise a hand grip portion 106. According to an example, the first handle portion 102 can include a first cover 108 attached to a first frame 110 and, similarly, the second handle portion 104 can include a second cover 112 attached to a second frame 114. The covers 108 and 112 can be ergonomically contoured, or otherwise suitably contoured, to assist a surgeon in manipulating the stapling instrument 100 within a surgical site. In various embodiments, the handle covers 108 and 112, for example, can include enlarged protrusions 109 and 113, respectively, which can facilitate the insertion of stapling instrument 100 into a surgical site. In various embodiments, the handle covers 108 and 112 can be made of plastic, lightweight materials, and/or any other suitable material, for example, while the handle frames 110 and 114 can be made of stainless steel, titanium, and/or any other suitable material, for example.

In various examples, the distal ends of handle portions 102 and 104 can comprise an end-effector 120 which can be configured to treat tissue within a surgical site, for example. In at least one example, the end-effector 120 can include a staple cartridge channel 122 configured to receive and/or retain a staple cartridge as described herein. According to examples, the staple cartridge channel 122 can comprise a one-piece elongated channel-shaped frame extending from the second handle portion frame 114 that can be made of a plastic, metal or any other suitable material. In at least one example, the staple cartridge channel 122 can include a pair of opposed, elongated side walls connected by a bottom wall. Along the rearward, or proximal, portion of the staple cartridge channel, a pair of spaced, upstanding side flanges can extend upwardly from opposed side walls. In various examples, the width of the staple cartridge channel 122 between side flanges can be greater than the width of the lower jaw member, or anvil, 130 extending from the first handle portion 102. In at least one embodiment, the distance between flanges can be configured to permit at least a portion of the anvil 130 to be received between side flanges when the stapling instrument is assembled for operation. According to one or more examples, each side flange of can include a notch, or recess, for example, which can be configured to receive one or more latch projections, for example, extending from the anvil 130, and/or any other suitable portion of the first handle portion 102. An example of a staple cartridge channel (e.g., as shown and described therein as staple cartridge channel 122) that can be used in one or more examples herein can be found, for example, in U.S. Pat. No. 7,954,686, issued Jun. 7, 2011, the contents of which is herein incorporated by reference in its entirety.

Figure 12:
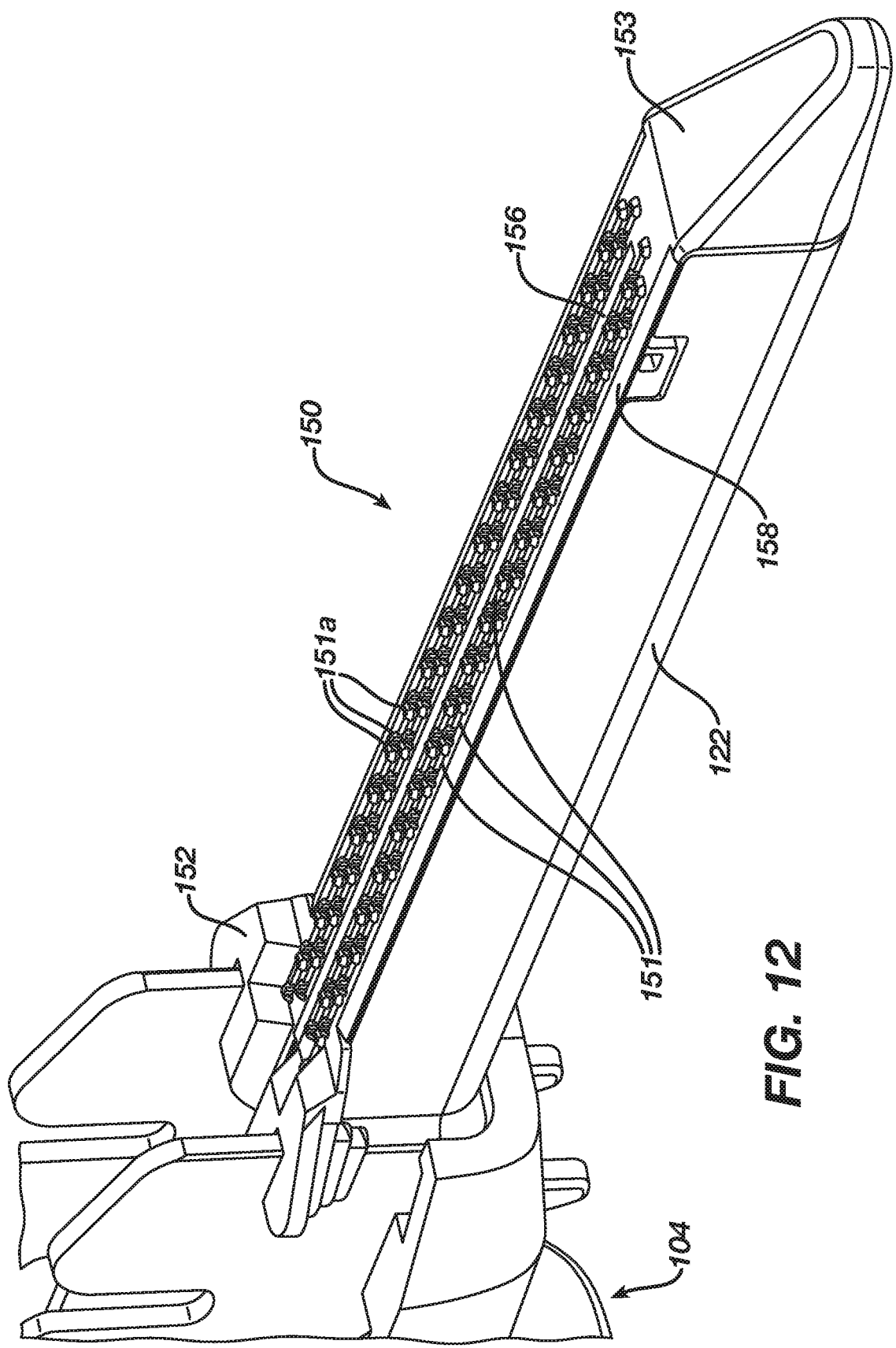
FIGS. 12-13 illustrate a perspective view of a staple cartridge assembly that can be included in the surgical stapling instrument in accordance with one or more examples.
Figure 13:
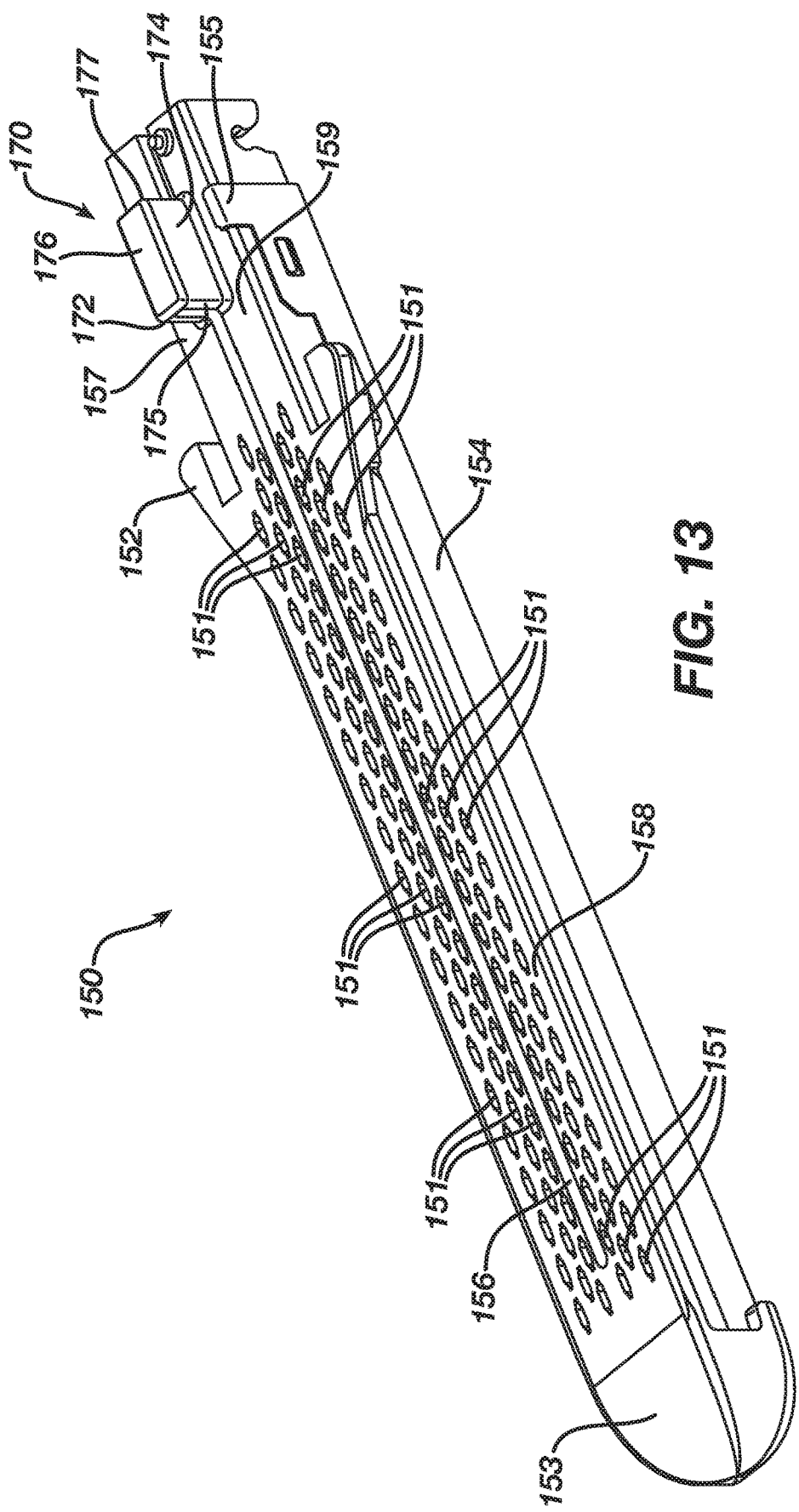
Figure 14:
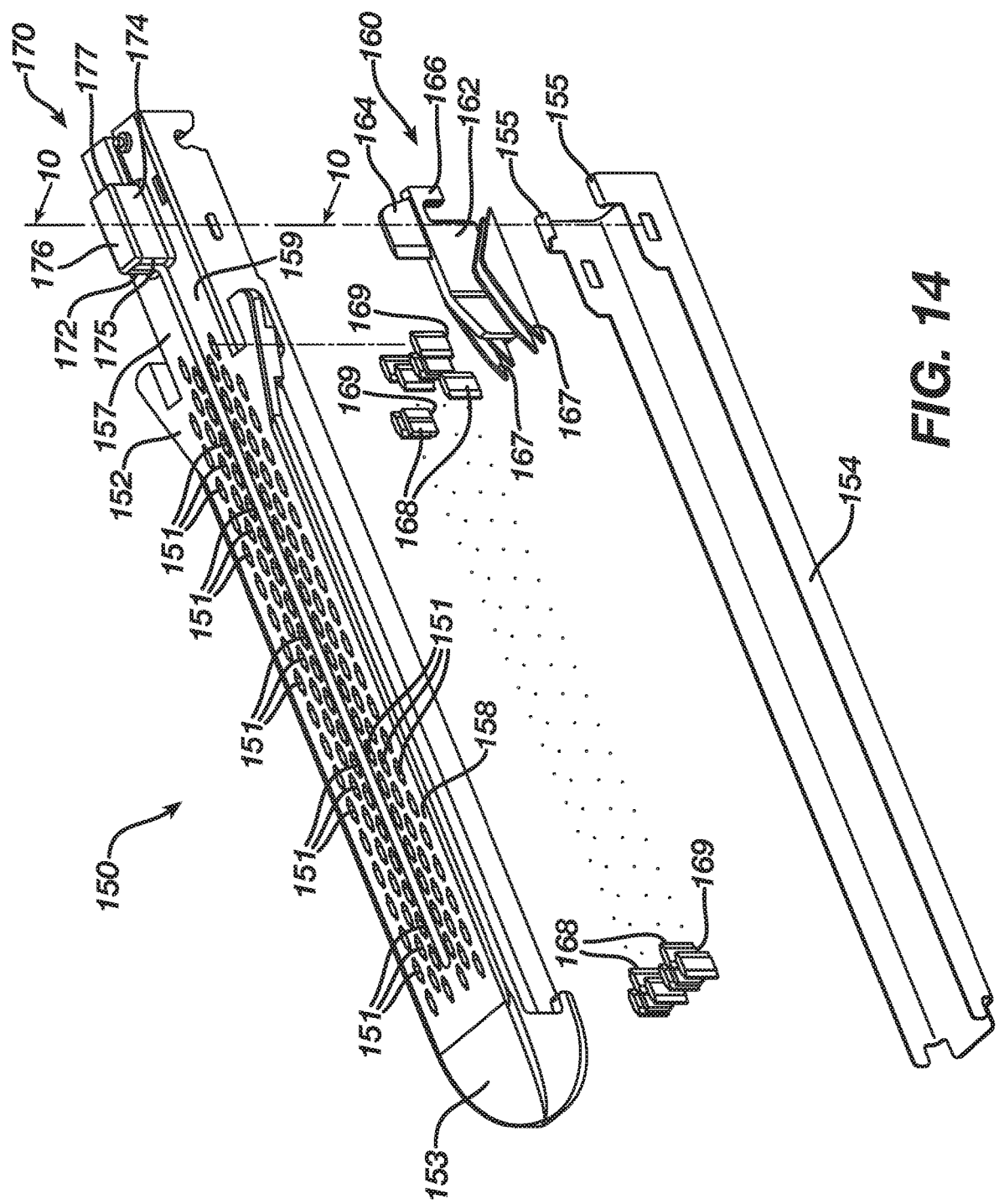
FIG. 14 illustrates an exploded view of the staple cartridge assembly, for example, of FIG. 13 in accordance with one or more examples.
Figure 15:
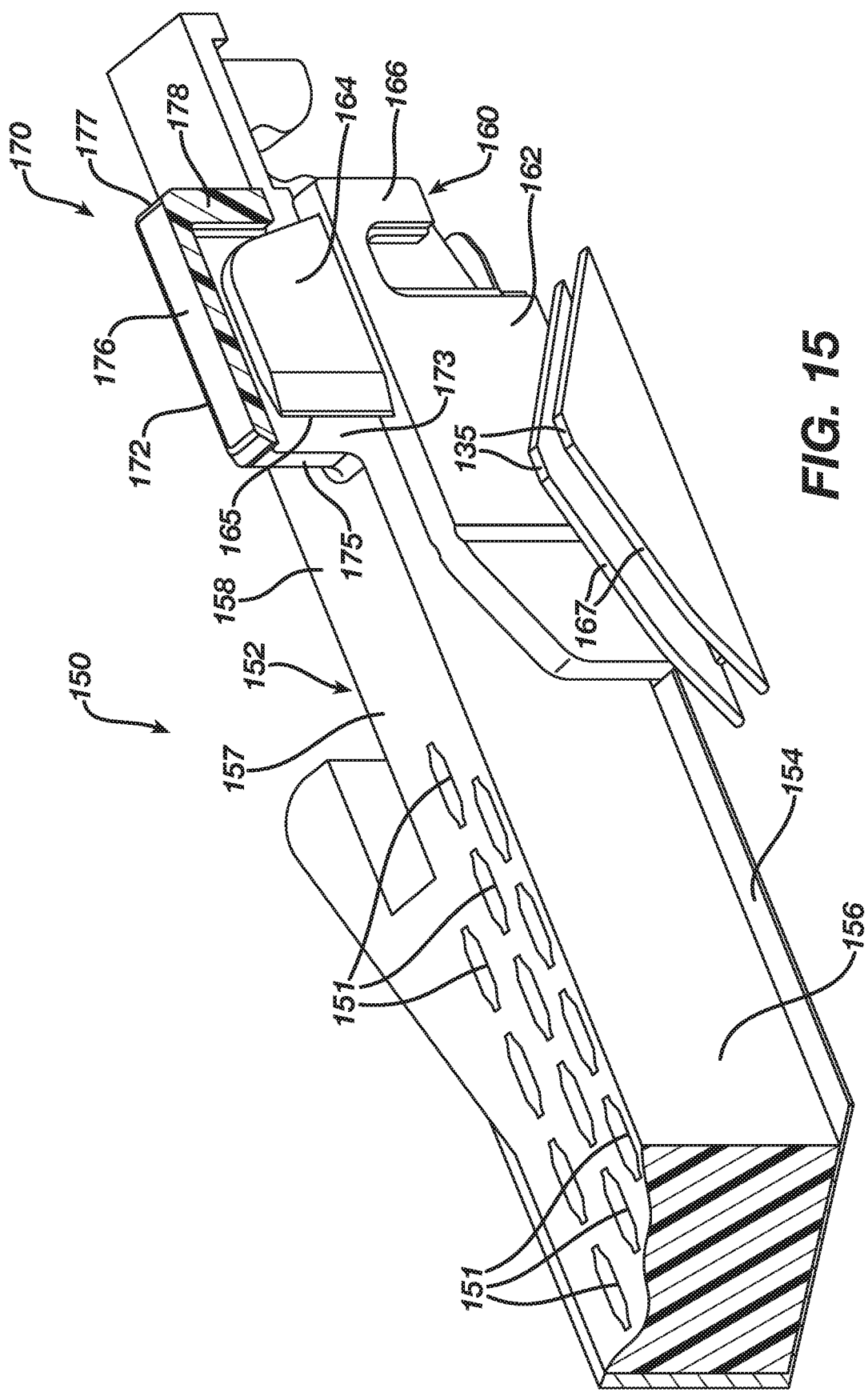
FIG. 15 is a cross-sectional view of the staple cartridge assembly taken along line 10-10 in FIG. 14.
Figure 16:
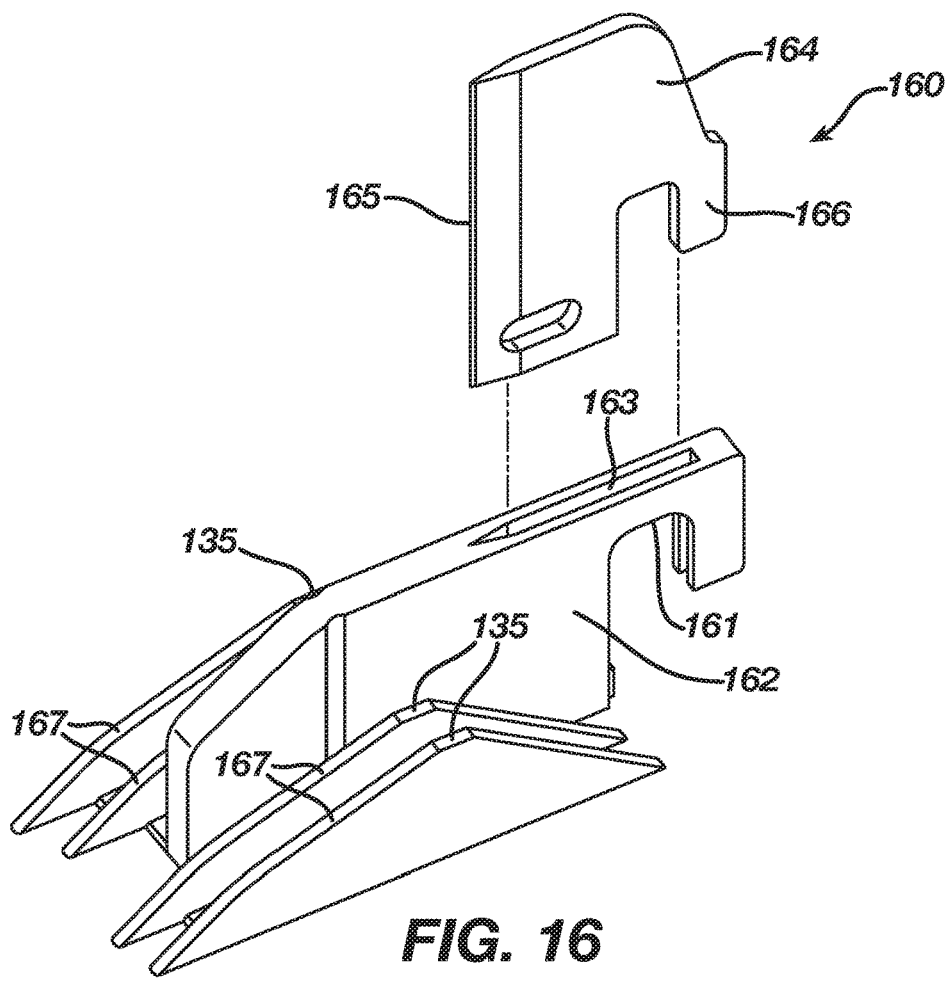
FIG. 16 is an exploded view of a staple sled and cutting member assembly that can be included in the staple cartridge assembly of FIGS. 12-13.
Figure 17:
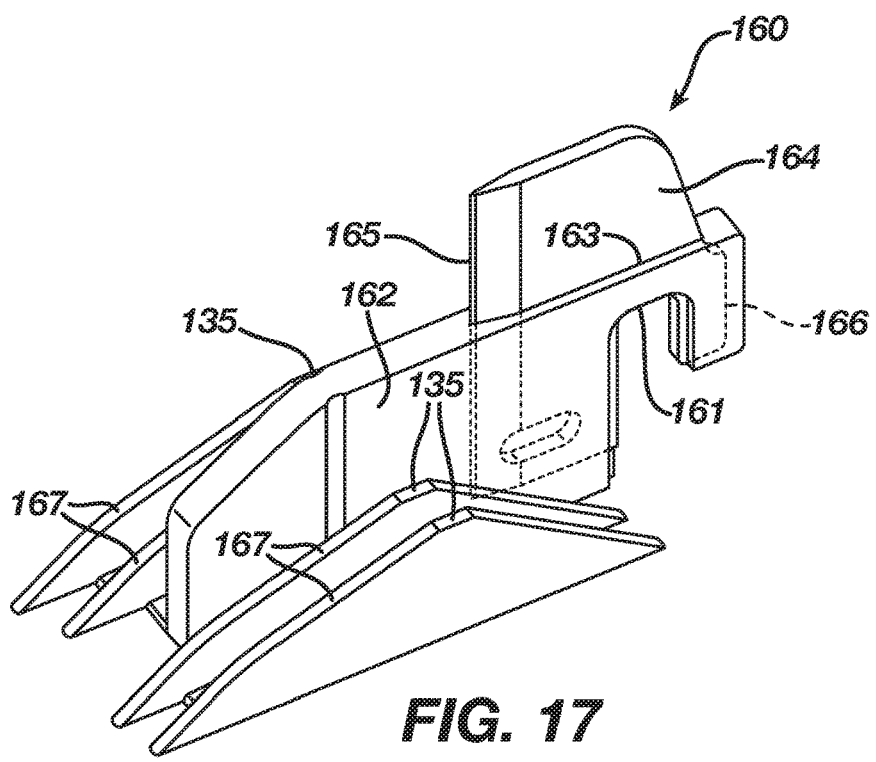
FIG. 17 is a perspective view of the staple sled and cutting member assembly of FIG. 16.

As described, the staple cartridge channel 122 can be configured to support and/or retain a staple cartridge, such as staple cartridge 150, for example, within the end-effector 120. In examples, the staple cartridge 150 can include one or more staples (not illustrated) removably stored therein. In various examples, referring to FIGS. 12-14, the staple cartridge 150 can include one or more staple cavities 151 which can be configured to store staples in any suitable arrangement, such as in at least two laterally-spaced longitudinal rows (e.g., as shown in FIG. 12) or at least three laterally-spaced longitudinal rows (e.g. as shown in FIGS. 13-14), for example. Further, in examples as shown in FIG. 12, the cavities 151 may have one or more tissue griping surface portions 151a, which can be protrusions (as shown), depressions, and/or the like used to help grip and manipulate tissue, adjacent to or surrounding at least a portion of the cavities 151 such as adjacent to or surrounding one or more proximal or distal ends of the cavities 151.

In at least one example, referring to FIGS. 13 and 14, the staple cartridge 150 can include a staple cartridge body 152 and pan 154. The staple cartridge 152 can be made of a plastic or any other suitable material in examples and can be molded therefrom and the pan 154 can be made of metal, and/or the like or any other flexible material. The staple cartridge body 152 and/or pan 154 can be configured to define a channel, or path, for slidably receiving a staple sled and/or cutting member therein. In at least one example, the pan 154 can include flexible arms 155, for example, which can be configured to engage the staple cartridge body 152 in a snap-fit and/or press-fit arrangement. Referring to FIGS. 14-17, the staple cartridge 150 can further include a staple sled assembly 160 (e.g., that can be made of plastic, metal, and/or the like) that can include a staple sled portion 162 and/or a cutting member 164. In various examples, the sled 162 can be made of metal, plastic, and/or the like and the cutting member 164 can be made of a metal or another material that can cut tissue. Further, in examples, the cutting member 164 can include a cutting edge 165 and lock arm 166, for example, where the lock arm 166 can be configured to be press-fit and/or snap-fit into an aperture 163 in the staple sled 162 when the cutting member 164 can be assembled to staple sled portion 162. In other various examples, the staple sled portion 162 can be integrally molded to the cutting member 164.

Further to the above, referring to FIGS. 12-15, the staple cartridge body 152 can include a slot, such as slot 156, for example. In examples, the slot 156 can be configured to receive at least a portion of the cutting member 164 therein, and/or any other portion of staple sled assembly 160 and a pusher bar assembly that can be actuated by a firing actuator 204. An example of a pusher bar assembly (e.g., as shown and described therein as pusher bar assembly 200), a firing actuator, and/or other components that can be used to fire staples and incise tissue that can be used in one or more examples herein can be found, for example, in U.S. Pat. No. 7,954,686, issued Jun. 7, 2011, the contents of which is herein incorporated by reference in its entirety. The slot 156 can be configured to permit cutting member 164 to be moved between first and second positions within the staple cartridge 150. In various examples, the slot 156 can be configured to permit the cutting member 164 to be moved between a proximal position (FIG. 14) and a distal position in order to incise tissue positioned between the staple cartridge 150 and anvil 130, for example.

As shown in examples such as FIGS. 14-17, the staple sled portion 162 can include a cam, ramp, or actuator, surfaces 167 that can be configured to engage staple drivers positioned within staple cartridge 150. In various examples, the staple cartridge 150 can include staple drivers 168 (e.g., that can be made of any suitable material such as plastic) that can be lifted, or slid, upwardly within staple cavities 151 by sled portion 162 such that the upward movement of staple drivers 168 can eject, or deploy, staples at least partially positioned within staple cavities 151 that can be formed by the anvil 130 to staple tissue. While the staple drives 168 can be, in fact, lifted vertically upwardly, the term upward, and the like, can refer to, mean, indicate, and/or the like that the staple drivers 168, for example, can moved toward the top surface, or deck, 158 of the staple cartridge and/or toward anvil 130, for example. In examples herein, each staple driver 168 can include one or more sloped surfaces 169 oriented at the same angle as a cam surface 167, and/or any other suitable angle that can provide a relatively flat, or at least substantially flat, sliding contact surface between the staple sled 162 and staple drivers 168. In various examples, a staple driver can be configured to deploy only one staple, while, in additional examples, a staple driver can be configured to simultaneously deploy two or more staples located in adjacent rows, for example. Additional examples of a surgical stapler and components thereof that can be included in the stapler or cutter 100 are disclosed in U.S. patent application Ser. No. 12/030,424, entitled SURGICAL STAPLING INSTRUMENT WITH IMPROVED FIRING TRIGGER ARRANGEMENT, which was filed on Feb. 13, 2008, the entire disclosure of which is incorporated by reference herein.

As such, in one or more examples, as described herein, a surgical stapling instrument can include a cutting member/staple sled assembly configured to incise tissue and deploy staples from a staple cartridge. In additional embodiments, a surgical stapling instrument may not include a cutting member. In at least one such example, a staple cartridge can include a staple sled positioned therein and/or a surgical instrument can be configured to move a staple sled into a staple cartridge to staple tissue, for example, without otherwise dissecting it. In other examples, a staple cartridge can include a staple sled positioned therein where a surgical instrument can include a cutting member movable into, or relative to, the staple cartridge. In at least one such example, the cutting member can be advanced into contact with the staple sled such that the cutting member and staple sled can be advanced together. Thereafter, the cutting member can be sufficiently retracted to allow the staple cartridge to be detached from the surgical instrument and replaced with another or new staple cartridge having another or new staple sled. Such examples may be useful when a staple sled may become worn or deformed during use. Other examples may be envisioned where a staple cartridge can include a cutting member positioned therein and a surgical instrument can include a staple sled movable into, or relative to, the staple cartridge. In at least one such example, similar to the examples described herein above, the staple sled can be advanced into contact with the cutting member such that the cutting member and staple sled can be advanced together. Thereafter, the staple sled can be sufficiently retracted to allow the staple cartridge to be detached from the surgical instrument and replaced with another or new staple cartridge having another or new cutting member. Such examples may be useful when a cutting member may become worn or deformed during use. In various examples, the staple cartridge can include a protective housing or cover configured to prevent, or at least reduce the possibility of, a surgeon or other clinician from touching the cutting member positioned within the staple cartridge while handling the staple cartridge, for example.

In various embodiments, further to the above, the staple cartridge channel 122 and/or staple cartridge 150, for example, can include one or more co-operating projections and/or recesses, for example, which can be configured to removably retain staple cartridge 150 within the staple cartridge channel 122. Once the staple cartridge 150 has been inserted into the staple cartridge channel 122, in various embodiments, the first handle portion 102 can be assembled to the second handle portion 104. In other various embodiments, the staple cartridge may be inserted into the staple cartridge channel after the first and second handle portions have been assembled together. In either example, referring to FIGS. 1-11, the first handle portion 102 and second handle portion 104 can include proximal ends 103 and 105, respectively, which can be assembled together such that the first and second handle portions can be rotatably or pivotably coupled to one another.

For example, the second handle portion 104 can include one or more latches, or projections, 111 extending therefrom at the proximal end 105. The latch or projection 111 can be made of metal, plastic, and/or the like and can be configured to be latched on or received by one or more pins 115 that can be made of metal, plastic, and/or the like in the first handle portion 102. In examples, the pin 115 can be defined in first handle frame 110 and the latch 111 can extend from a pin, post, protrusion, and/or the like such as pin 111b that can be part of or can extend from the second handle frame 114, for example such that the latch 111 can rotate via such a pin, post, protrusion, and/or the like to enable the latch to be snapped around or onto the pin 115. The latch 111 can be spring loaded and/or biased. In examples, to assemble first handle portion 102 and second handle portion 104, the first and second handle portions 102, 104 may be snapped together such that the latch 111 may rotate and snap over the pin 115 to be received thereby. According to examples, the latch 111 also can be connected to a latch release button 111a that can be depressed to push the latch 111 off or away from the pin 115 thereby enabling the first and second handle portions 102, 104 to be detached from each other at the proximal ends 103, 105. In the examples shown, the latch release button 111a can be included in the first and/or second handle portions 102, 104, respectively.

Figure 3:
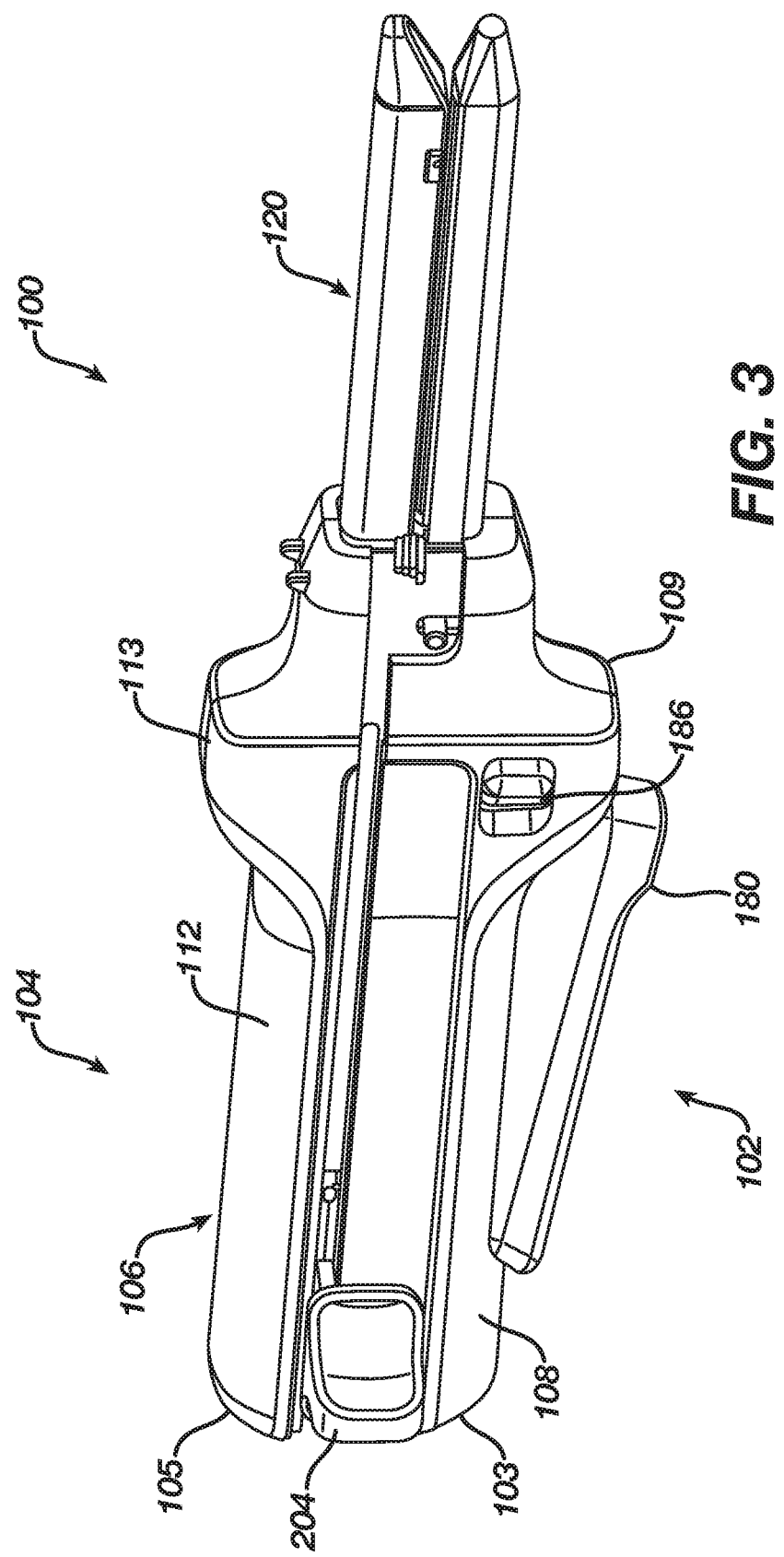
Figure 4:
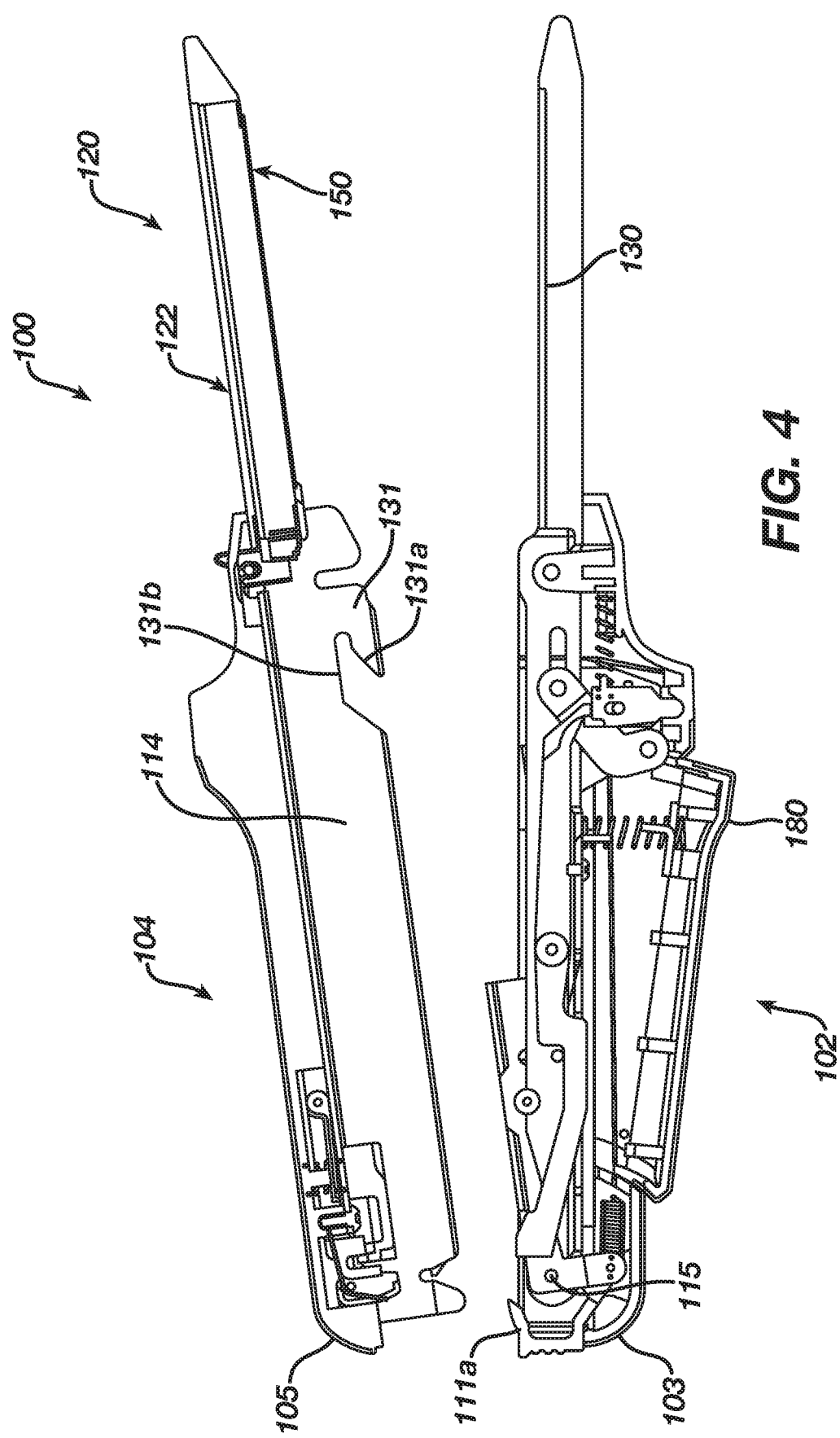
Figure 5:
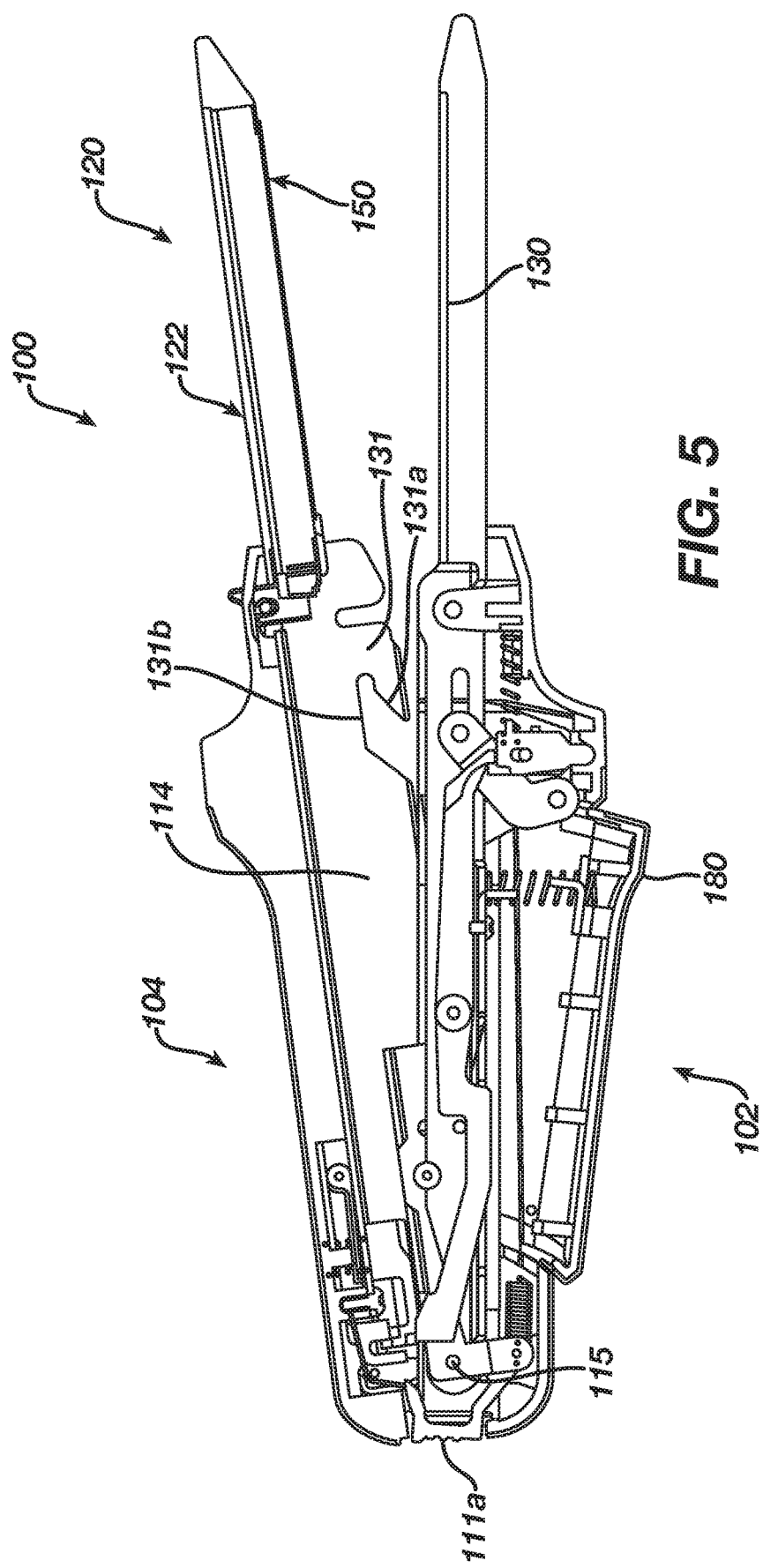
Figure 6:
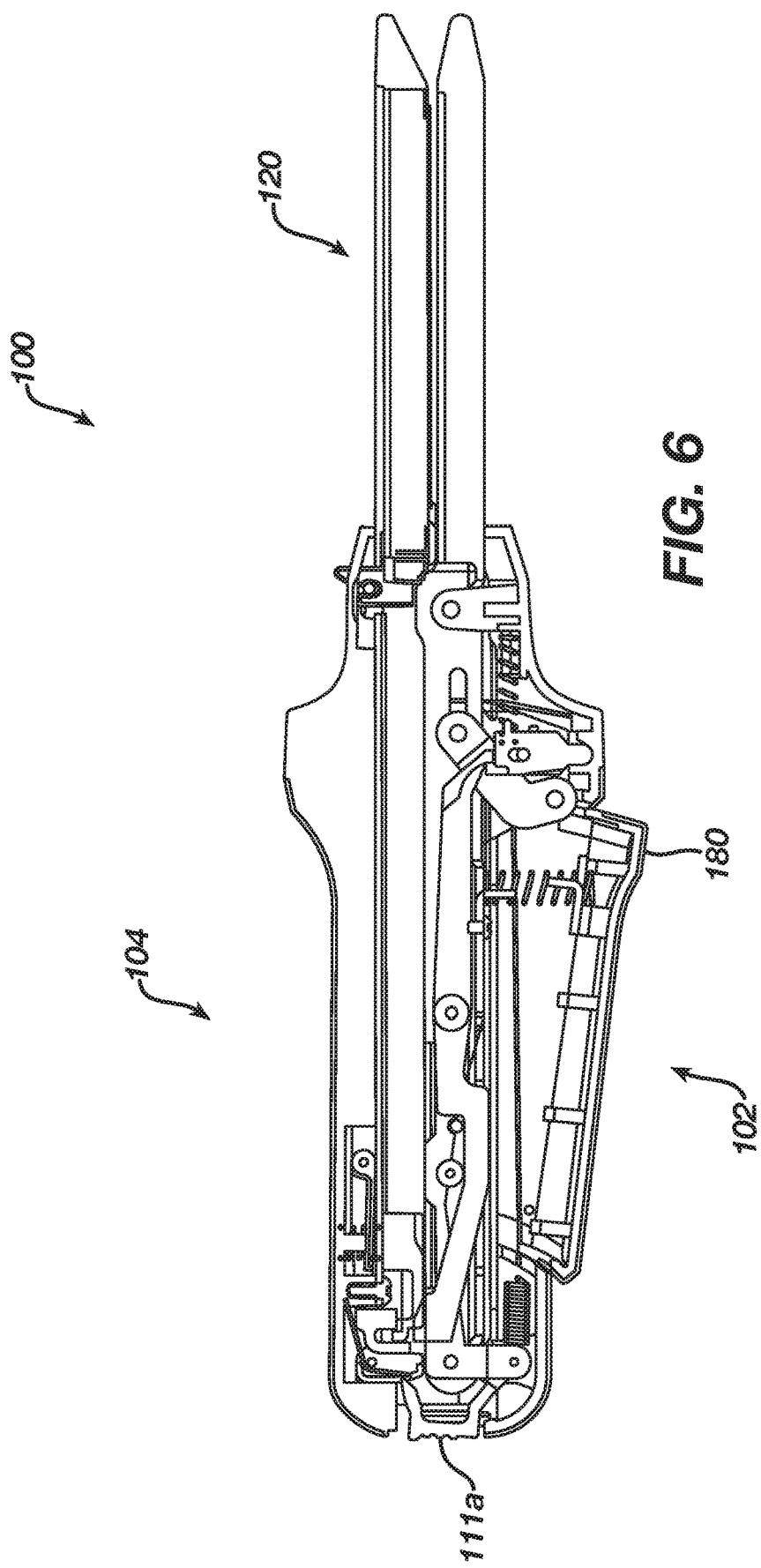

In various examples, the second handle portion 104 can be rotated toward the first handle portion 102 and/or the first handle portion 102 can be rotated toward the second handle portion 104 such that the anvil 130 can be moved into position relative to staple cartridge 150. For example, the first handle portion 102 can be rotated towards the second handle portion 104 and/or the first and second handle portions 102, 104 can be rotated toward each other as shown in FIGS. 1-11 such that the anvil 130 and staple cartridge 150 may be moved toward and in proximity to each other (e.g., into a closed position) to clamp tissue therebetween as shown in FIGS. 3 and 6. To provide such rotation between the first and second handles 102, 104, a latch 111 can be provided at the proximal ends 103, 105 respectively. In examples, the latch 111 and pin 115, when engaged with one another, can comprise a pivot about which one or both of the first and second handle portions 102, 104 can be moved relative to each other. In various example, the second handle portion 104 can be moved relative to the first handle portion 102 such that anvil 130 can be moved into a closed opposition to the staple cartridge 150 (e.g., a closed position). In examples, to detach the first and second handle portions 102, 104, for example, after use, to reposition the linear cutter or stapler 100, and/or the like, the surgeon or user can press the latch release 111a thereby causing the proximal latch 111 to detach from the pin 115 and decoupling the first and second handle portions 102, 104.

Further, in examples shown, the second handle portion 104 may include a latch projection 131 extending from the second handle frame 114. The latch projection 131 can be integrally formed in the second handle frame in one example. The latch projection 131 can be configured to receive a linkage or other protrusion (e.g., 184) that can be part of the first handle portion 102 such that the anvil 130 and staple cartridge 150 can be clamped together and locked in the closed position. In examples, the latch projection 131 includes a ramp 131a and a recess or opening 131b formed thereby. The ramp 131a can be configured to guide the linkage or other protrusion into the recess or opening 131b such that the first and second housing portions 102, 104 can be clamped together in the closed position.

Figure 7:
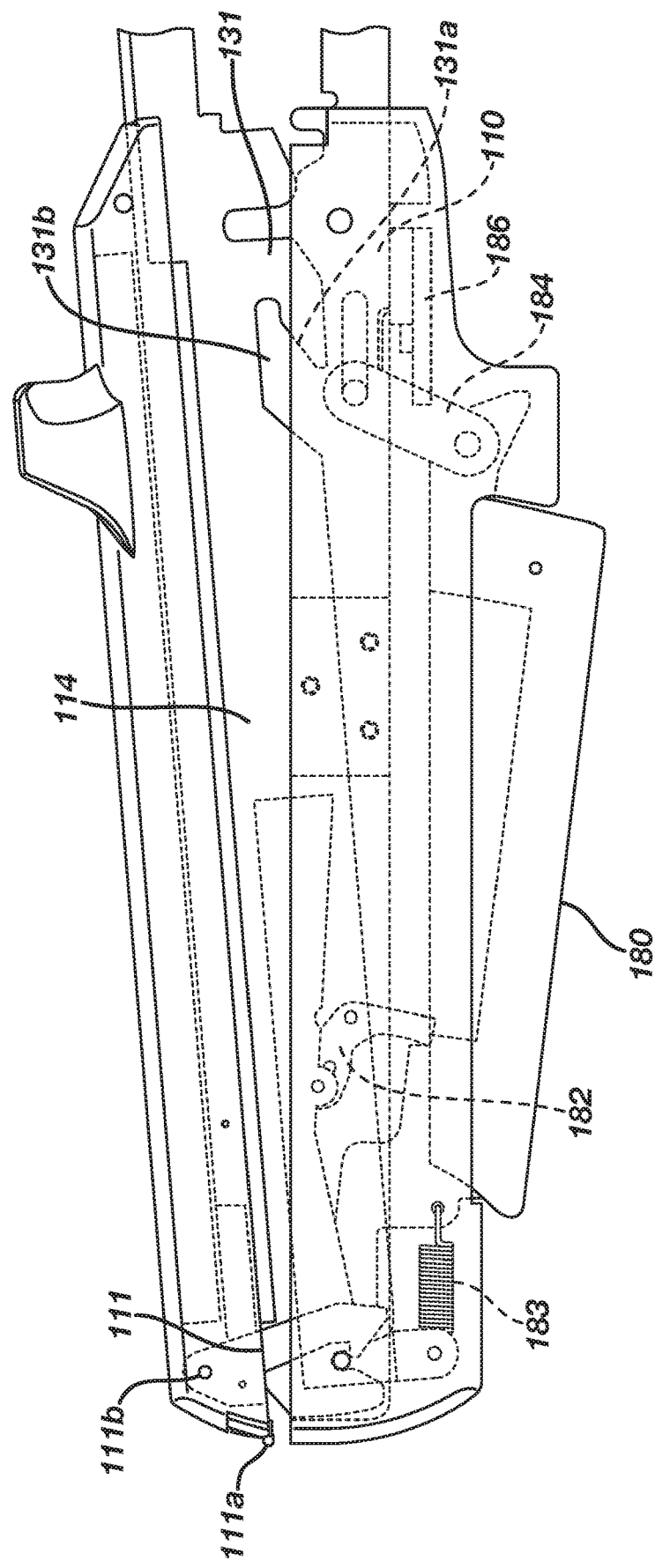
Figure 10:
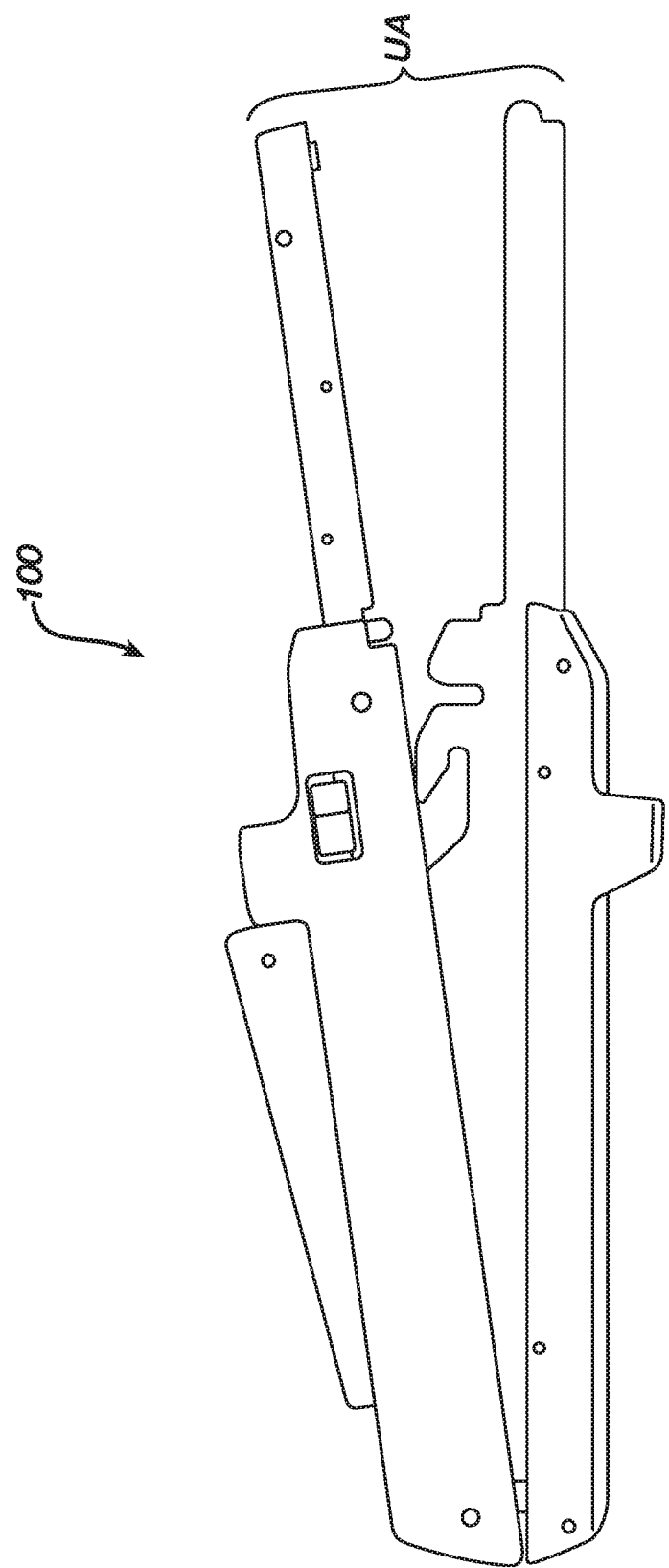
Figure 11:
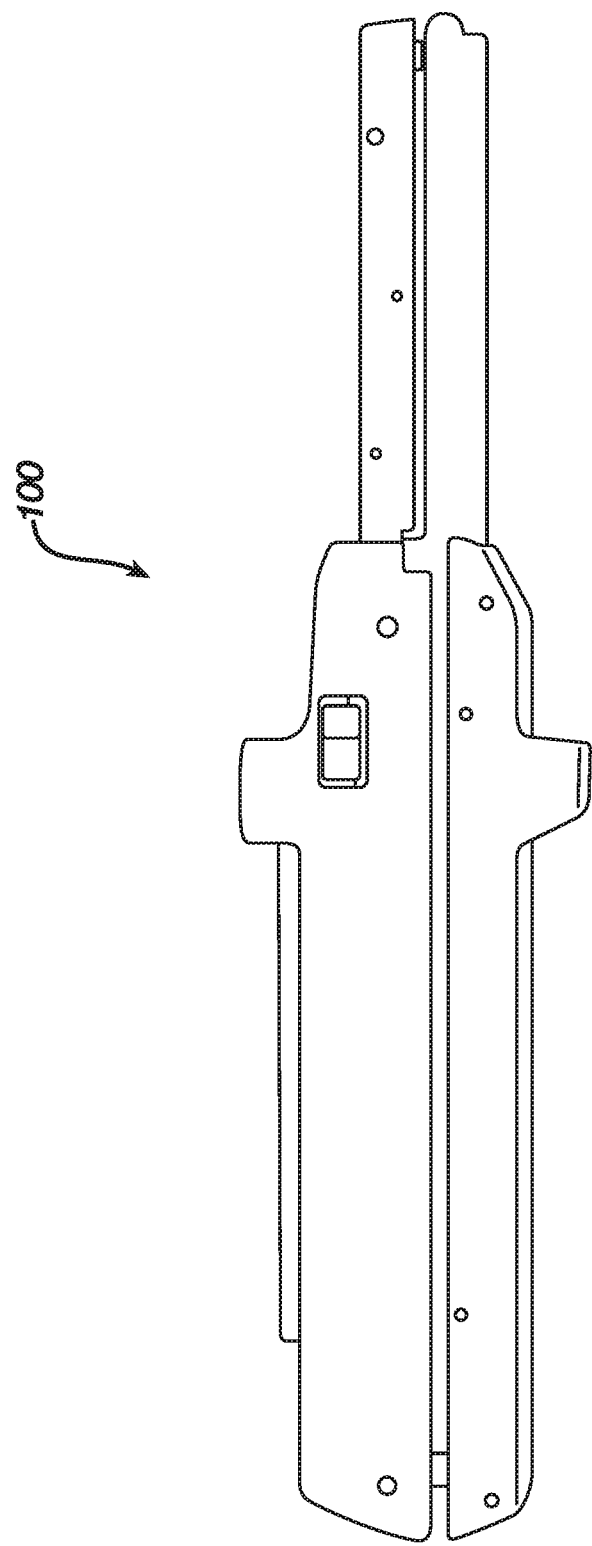

As shown, the first handle portion 102 can include a clamp arm 180, a clamp arm latch 182, a clamp arm spring 183, an over center link or linkage 184, and/or a clamp arm release 186 that can be mechanically connected to each other or in mechanical cooperation with each other and can be actuated to engage the latch projection 131 to, for example, clamp or lock the first and second handle portions 102, 104 such that the anvil 130 and staple cartridge 150 can be in a closed position and release the first and second handle portions 102, 104, the anvil 130, and the staple cartridge 150 from the closed position as described herein. In examples, the clamp arm 180 can be made of a plastic and/or any other suitable material. For example, the clamp arm 180 can be locked open or remain undepressed (e.g., be in an unengaged position or remain in such an unengaged position) via the clamp arm latch 182 and the clamp arm spring 183, which can bias the clamp arm 180 such that the first and second handle portions 102, 104 can remain in an open position as shown in FIGS. 7 and 10 (e.g., the staple cartridge 150 and anvil 130 can have a space or aperture therebetween such as the in-use aperture UA) as shown in FIG. 7.

Figure 8:
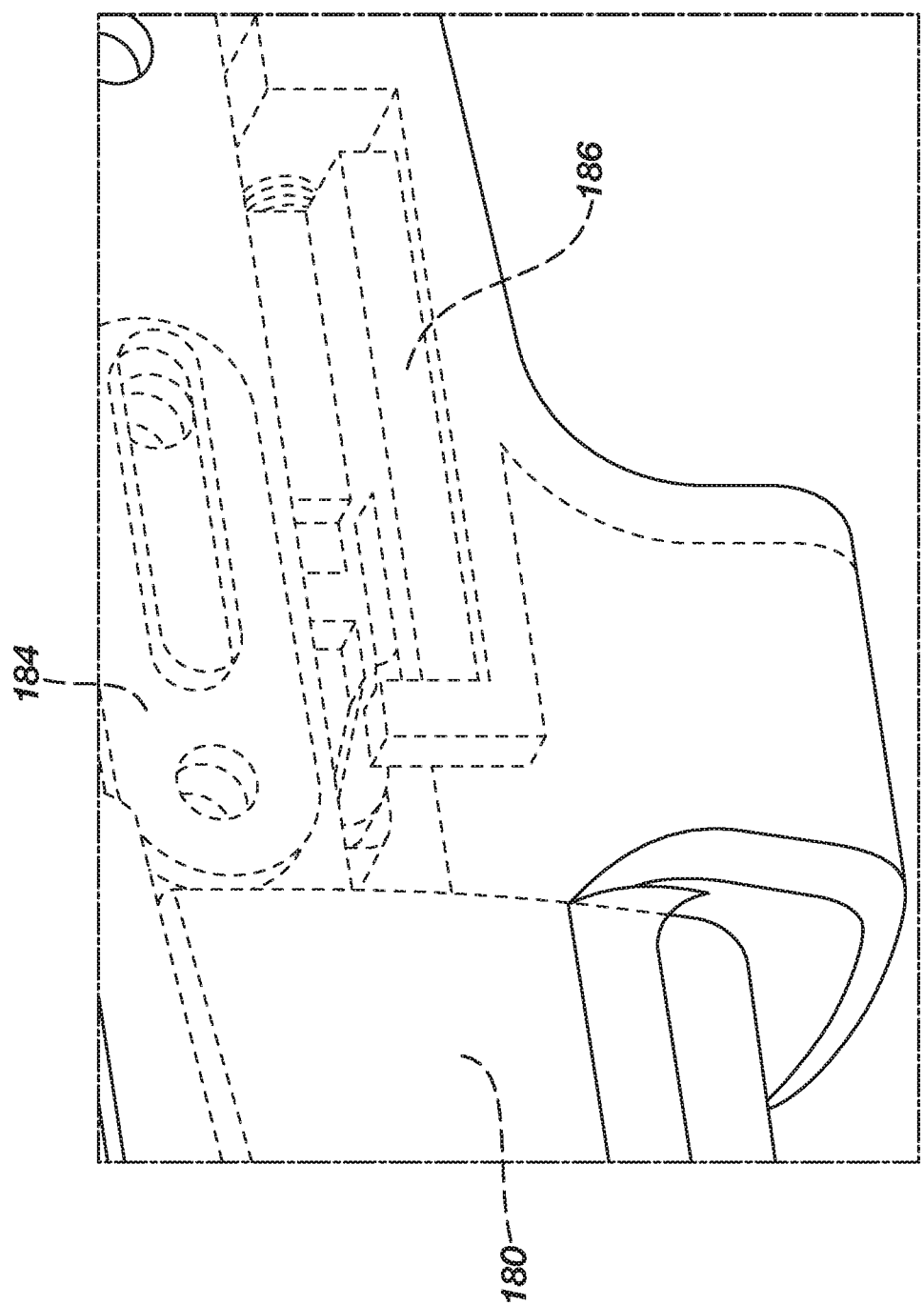

Further, in one or more examples, the clamp arm latch 182 can release the clamp arm 180 when the first and second handle portions 102, 104 sections of the linear stapler 100 are in proximal position to each other. In examples, the clamp arm 180 can be connected to the over center link or linkage 184 such that when the clamp arm 180 may be depressed, the over center link or linkage 184 can move from an unengaged position as shown in FIG. 7 to an engaged position as shown in FIG. 8 and engage the latch projection 131 to lock or clamp the first and second handle portions 102, 104 such that the anvil 130 and staple cartridge 150 are in the closed position.

According to one or more examples, the clamp arm 180 can be unlocked from a closed position via the clamp arm release 186. For example, the clamp arm release 186 can be spring loaded, can be slidable, and/or the like and can include a ramped surface, pin, and/or the like to engage with a portion of the clamp arm 180 as shown in FIGS. 7-8. In an example, after actuating or depressing the clamp arm 180 the clamp arm release 186 may move from an unengaged position as shown in FIG. 7 to an engaged position (e.g., it may be engaged with the clamp arm 180 and the over center link or linkage 184) as shown in FIG. 8. Further, according to an example, upon actuating the clamp arm release 186 (e.g., by sliding it proximally), the clamp arm 180 may return from the closed depressed position shown in FIGS. 3, 6, 8, and 11 to the open position shown in FIGS. 1-7 and 9-10. The clamp arm release 186 can also move from the engaged position shown in FIG. 8 back to the unengaged position shown in FIG. 7 as described herein.

Figure 9:
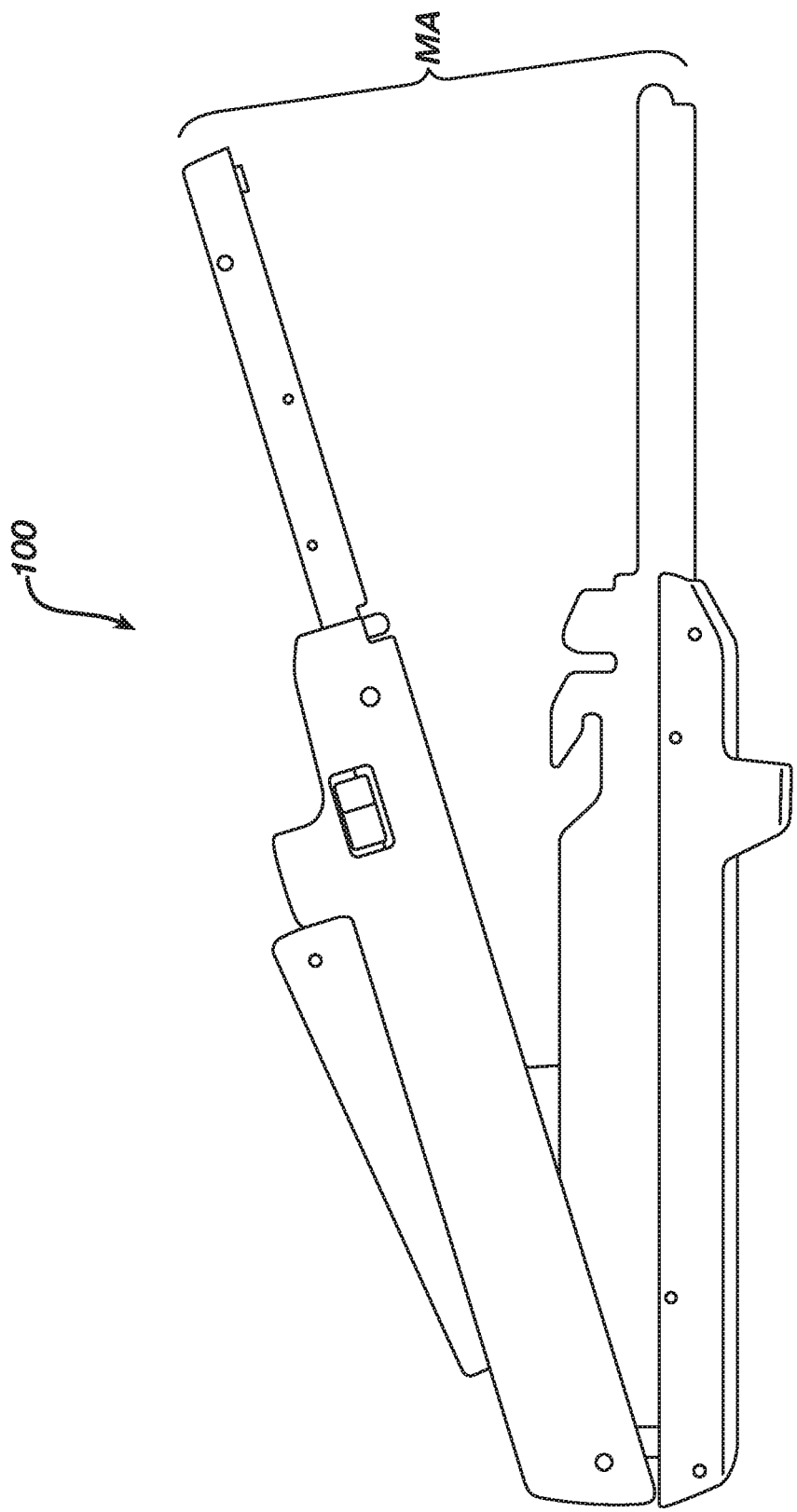

Further, in examples, the surgical instrument 100 can provide a limit on its jaw aperture based on its proximal latching (e.g., that can be provided by the latch 111 and pin 115 described herein). For example, as shown in FIG. 9, upon latching the proximal ends 103, 105 as described herein, a maximum jaw aperture MA can be provided by the surgical instrument 100. The first and second housing portions 102, 104 can then be moved toward or relative to each other as described herein such that, as shown in FIG. 10, an in-use aperture UA can be provided by the surgical instrument 100. The in-use aperture UA can be the aperture or range of distance between the jaws after moving the first and second housing portions 102, 104 relative to each other such that they can be clamped but prior to actually engaging the clamp arm 180 as described herein to close the jaws and place the surgical instrument 100 in the closed position (e.g., the closed position being where the handle portions 102, 104 can be locked by the clamp arm 180 and the anvil 130 and staple cartridge 150 can be in proximity to each other to staple and incise tissue as described herein).

As such, in examples described herein, the proximal ends 103, 105 of the first and second handle portions 102, 104 can be connected with a spring loaded latch such as the proximal latch 111, the clamp arm 180 can engage a clamp pin such as the latch projection 131 through an over center mechanism such as the over center link or linkage 184, the clamp arm 180 can be biased opened via a clamp arm spring such as the clamp arm spring 183 and a clamp arm latch such as a clamp arm latch 182 and can be disengaged with a slidable latch such as the clamp arm release 186. Further, according to examples herein, the first and second handle portions 102, 104 can be clamped together by a surgeon using one hand using the clamp arm 180 and assembly associated therewith as shown and described, which can be contrary to current linear cutters or staplers in which a surgeon typically uses both hands and/or a surgical assistant helps as well.

To actuate the liner cutter or stapler 100, in one or more examples (e.g., as shown in FIGS. 2-3 and 5-6), the first and second handle portions 102, 104 at the proximal ends 103, 105 can be connected to each other via the latch 111 and pin 115 as described herein. For example, as shown in FIGS. 1-2, 4-5, and 7, a surgeon or user of the linear cutter or stapler 100 can position the proximal ends 103, 105 near each other and compress or squeeze them together such that the proximal latch 111 can pivot around and snap onto the pin 115 as described herein. In an example, this may secure lock or secure the first and second handle portions 102, 104 together at the proximal ends 103, 105.

Further, the second handle portion 104 can be moved relative (e.g., by the surgeon or user) to first handle portion 102 and/or vice versa. The surgeon or user can squeeze or actuate the clamp arm 180 (e.g., after moving the first and second handle portions to the position shown in FIG. 7) such that latch projections 131 extending from the second handle portion 104 can receive the over center link or linkage 184. For example, upon squeezing the clamp arm 180, the over center link or linkage 184 can move distally up and/or along the ramp 131a and at least a portion thereof can be received into the recess 131b (e.g., as shown in FIG. 8) thereby locking the clamp arm 180 in an engaged position and securing the first and second handle portions 102, 104 such that the anvil 130 and staple cartridge 150 are in a closed position as shown in FIGS. 3, 6, 8, and 11. In various examples, upon squeezing or actuating the clamp arm 180 to the engaged position and thereby clamping the first and second housing portions 102, 104 together in the closed position (e.g., where the anvil 130 and staple cartridge 150 are in proximity to each other or can clamp together on tissue), the linear cutter or stapler 100 can then be fired by pushing the firing actuator 204 distally in examples or thereby engaging the firing actuator 204. For example, once the anvil 130 and staple cartridge 150 have been sufficiently positioned and the first and second housing positions 102, 104 are in the closed position, the tissue positioned intermediate anvil 130 and staple cartridge 150 can be stapled and/or incised. To staple and/or incise the tissue, in examples, a pusher bar assembly (e.g., such as the pusher bar assembly 200 described in U.S. Pat. No. 7,954,686) can be configured to advance and/or retract staple sled assembly 160 within staple cartridge 150, for example. In at least one example, the pusher bar assembly can include a pusher bar (e.g., such as the pusher bar 202 described in U.S. Pat. No. 7,954,686) and the firing actuator 204 where the firing actuator 204 can be configured to move pusher bar and staple sled assembly 160 distally to deploy staples from staple cartridge 150 and deform the staples against anvil 130 as described herein. The firing actuator 204 (e.g., via the pusher bar) can also be configured to move the cutting member 164 distally to incise tissue when the firing actuator 204 may be advanced distally or otherwise actuated. For example, the surgeon or user can interact with the firing actuator 204 by moving the firing actuator 204 distally on one side or the other of the first and second housing portions 102, 104 to cause the pusher bar, staple sled assembly 160, and/or cutting member 164 to move or advance distally thereby deploying the staples into the tissue and/or incising the tissue.

In examples, after incising and/or stapling the tissue, in examples, the firing actuator 204 can be can be configured to move pusher bar, staple sled assembly 160, and/or the cutting member 164 proximally thereby completing a stapling and/or cutting procedure. For example, the surgeon or user can move the firing actuator 204 proximally back to its pre-fired position to retract the pusher bar, the sled assembly 160, and the cutting member 164. Upon retracting such components or moving the proximally back to a pre-fired position (e.g., as shown in FIG. 3), the stapling instrument 100 (e.g., the linear cutter or stapler 100) can be opened to add another cartridge to staple and/or incise additional tissue and/or to remove the instrument after finishing the procedure being performed. For example, the surgeon can move the firing actuator 204 back to its pre-fired position thereby retracting the pusher bar, staple sled, cutting member, and/or the like. The surgeon, in examples, can then interact with or actuate the clamp arm release 186 (e.g., by sliding it proximally) thereby causing the over center link or linkage 184 to move out of the recess 131*b* and proximally down and/or along the ramp 131*a* to move back from the engaged position shown in FIG. 8 to the unengaged position shown in FIG. 7. The clamp arm 180 may also return from the closed depressed position shown in FIG. 8 and FIGS. 3 and 6 to the open position shown in FIG. 7 and FIGS. 1-2 and 4-6. According to examples, the surgeon can also interact with the latch release button 111*a* by pressing it thereby causing the latch 111 to push off or away from the pin 115 thereby enabling the first and second handle portions 102, 104 to be detached from each other at the proximal ends 103, 105 and return back to the positions shown in FIGS. 1 and 3.

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument can comprise: a handle comprising first and second handle portions, one of the first and second housing portions comprising a proximal latch and a proximal latch pin, the proximal latch and proximal latch pin being configured to lock the first and second housing portions together at proximal ends thereof, one of the first and second housing portions further comprising a latch projection, a clamp arm, an over center linkage, the latch projection and over center linkage being configured to lock the surgical instrument in a closed position when the clamp arm is engaged or in an engaged position.

Example 2

One of first and second housing portions of a surgical instrument can comprise a proximal latch release, the proximal latch release being configured to release or detach the first and second housings at the proximal ends thereof after being locked together.

Example 3

One of first and second housing portions of a surgical instrument can comprise a clamp arm release, the clamp arm release being configured to unlock the surgical instrument form the closed position when the clamp arm is engaged.

Example 4

One of first and second housing portions of a surgical instrument can comprise a clamp arm latch and clamp arm spring, the clamp arm latch and clamp arm spring being configured to bias the clamp arm in an unengaged position.

Example 5

One of first and second handle portions of a surgical instrument can comprise first and second frames, respectively.

Example 6

One of first and second frames of a surgical instrument can comprise a staple channel extending therefrom.

Example 7

A staple channel of a surgical instrument can be configured to receive a staple cartridge therein.

Example 8

One of first and second frames of a surgical instrument can comprise an anvil extending therefrom.

Example 9

A surgical instrument can comprise one or more of the following: a pusher assembly, a cutting member, and a firing actuator.

Example 10

A firing actuator of a surgical instrument can be configured to move a pusher assembly and cutting member from a proximal position to a distal position to incise tissue and deploy staples from a staple cartridge such that the staples can form in the tissue via an anvil when a clamp arm may be engaged or in an engaged position.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A surgical instrument, the surgical instrument comprising:
   a handle comprising first and second handle portions, one of the first and second housing portions comprising a proximal latch and the other of the first and second handle portions comprising a proximal latch pin, the proximal latch and proximal latch pin being configured to engage with each other to lock the first and second housing portions pivotally together at proximal ends thereof,
   the second housing portion further comprising a latch projection and the first housing portion further comprising a clamp arm and an over center linkage pivotally connected to the clamp arm at a first end and slidably connected to the first handle portion at a second end, the latch projection and over center linkage being configured to engage with each other when the clamp arm is depressed to lock the surgical instrument in a closed position when the first and second handle portions are clamped together,
   wherein the clamp arm being depressed causes the second end of the over center linkage to slide relative to the first handle portion from an unengaged position to an engaged position where the over center linkage engages the latch projection,
   wherein the first handle portion further comprises a clamp arm release slidable between engaged and unengaged positions and biased towards its engaged position, wherein the clamp arm release is retained in its undepressed position when the over center linkage is in its unengaged position and the clamp arm release is permitted to move to its engaged position once the clamp arm is moved to its depressed position, and wherein the clamp arm release is configured to retain the over center linkage in its engaged position and the clamp arm in its depressed position when the clamp arm release is in its engaged position and permits the over center linkage to move to its unengaged position and the clamp arm to its undepressed position once the clamp arm release has returned to its unengaged position.

2. The surgical instrument of claim 1, wherein one of the first and second housing portions further comprises a proximal latch release, the proximal latch release being configured to detach the proximal latch from the proximal latch pin to release or detach the first and second housing portions at the proximal ends thereof after being locked together.

3. The surgical instrument of claim 1, wherein the first housing portion further comprises a clamp arm latch and clamp arm spring, the clamp arm latch and clamp arm spring being configured to bias the clamp arm away from its depressed position.

4. The surgical instrument of claim 1, wherein the first and second handle portions further comprise first and second frames, respectively.

5. The surgical instrument of claim 4, wherein one of the first and second frames comprise a staple channel extending therefrom.

6. The surgical instrument of claim 5, wherein the staple channel is configured to receive a staple cartridge therein.

7. The surgical instrument of claim 5, wherein one of the first and second frames comprise an anvil extending therefrom.

8. The surgical instrument of claim 7, further comprising one or more of the following: a pusher assembly, a cutting member, and a firing actuator.

9. The surgical instrument of claim 8, wherein the firing actuator is configured to move the pusher assembly and cutting member from a proximal position to a distal position to incise tissue and deploy staples from the staple cartridge such that the staples can form in the tissue via the anvil when the clamp arm is depressed.

* * * * *